(12) United States Patent
McCully

(10) Patent No.: US 11,911,615 B2
(45) Date of Patent: Feb. 27, 2024

(54) SYSTEMS AND METHODS FOR ASSESSING RESPIRATORY FUNCTION

(71) Applicant: University of Georgia Research Foundation, Inc., Athens, GA (US)

(72) Inventor: Kevin K. McCully, Athens, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 210 days.

(21) Appl. No.: 17/220,625

(22) Filed: Apr. 1, 2021

(65) Prior Publication Data

US 2021/0308453 A1    Oct. 7, 2021

Related U.S. Application Data

(60) Provisional application No. 63/003,707, filed on Apr. 1, 2020.

(51) Int. Cl.
*A61N 1/36* (2006.01)
*A61N 1/04* (2006.01)

(52) U.S. Cl.
CPC ......... *A61N 1/3601* (2013.01); *A61N 1/0456* (2013.01)

(58) Field of Classification Search
None
See application file for complete search history.

(56) References Cited

U.S. PATENT DOCUMENTS

2016/0310730 A1* 10/2016 Martins .............. A61N 1/36031
2017/0333706 A1* 11/2017 Schepis ................ A61N 1/3601

* cited by examiner

*Primary Examiner* — Catherine M Voorhees
*Assistant Examiner* — Elizabeth K So
(74) *Attorney, Agent, or Firm* — Thomas|Horstemeyer, LLP

(57) ABSTRACT

In one embodiment, an assessment system includes an electrical stimulation device configured to generate current, stimulation electrodes configured to apply the current generated by the electrical stimulation device to a neck of a subject at a location that results in stimulation of a phrenic nerve of the subject, a movement sensor configured to sense movement of an upper abdomen of the subject caused by twitching of a diaphragm of the subject responsive to the stimulation of the phrenic nerve, and a controller configured to receive data sensed by the movement sensor, analyze the received data to evaluate the activity of the diaphragm, and generate an assessment of the subject's respiratory function or phrenic nerve.

20 Claims, 4 Drawing Sheets

SYSTEMS AND METHODS FOR ASSESSING RESPIRATORY FUNCTION

BACKGROUND

Respiratory dysfunction and respiratory failure are severe medical issues that can be caused by a variety of conditions. Regardless of the cause, these issues can cause significant morbidity and can profoundly impact both short-term and long-term patient survival. As such, it is critical to assess the respiratory function of at-risk individuals in order to prevent respiratory dysfunction and failure.

Current methods of clinically assessing respiratory function are subjective and/or contingent upon patient participation. This leads to variability that can create uncertainty in outcomes and, therefore, such methods fail to meet the clinical need. An inexpensive means for performing objective assessments of respiratory function that can be used to stratify at-risk populations would be of immense clinical interest in outpatient, inpatient, and critical care settings.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have an inexpensive means for performing objective assessments of respiratory function. Examples of such means are disclosed herein in the form of respiratory function assessment systems. In some embodiments, a respiratory function assessment system comprises an electrical stimulation device configured to generate electrical current, stimulation electrodes configured to deliver the current to a neck of a subject adjacent one of his or her phrenic nerves, a movement sensor configured to sense rapid contractions (twitches) of the subject's thoracic diaphragm in response to the applied current, and a controller configured to control the electrical stimulation device, and receive and store measurements collected by the movement sensor. In some embodiments, the movement sensor comprises a triaxial accelerometer that measures accelerations of the abdomen in three orthogonal directions and the controller comprises a portable, wireless computing device, such as a smart phone or tablet device. During a respiratory function evaluation, the phrenic nerve is stimulated for several minutes by the applied current while accelerations of the abdomen are simultaneously measured. The magnitudes of the twitches measured at the beginning of the test (prior to fatigue) and those measured at the end of the test (after fatigue sets in) provide an indication of the endurance of the subject's diaphragm and, therefore, strength of the subject's respiratory function. In some embodiments, an endurance index can be calculated and presented to a medical professional on the controller that provides a numeric quantification of respiratory function on a scale from 0 to 100%.

In the following disclosure, various specific embodiments are described. It is to be understood that those embodiments are example implementations of the disclosed inventions and that alternative embodiments are possible. Such alternative embodiments include hybrid embodiments that include features from different disclosed embodiments. All such embodiments are intended to fall within the scope of this disclosure.

The thoracic diaphragm is the primary inspiratory muscle of the body both at rest and during exercise. It is, therefore, essential for respiration. Because of the role that the diaphragm plays, it should be considered when assessing respiratory function. Accordingly, the disclosed systems and methods are configured to facilitate such assessment.

Skeletal muscle fatigue is a common issue in certain populations, and increased fatigability of the diaphragm is problematic considering its role in inspiration. Muscle fatigability is a good indicator of muscle quality and can be assessed to determine respiratory health and function. One way to assess muscle fatigability is by having the subject perform a diaphragm endurance test. If a suitable test were available, it would provide an objective method of directly assessing respiratory function.

Figure 1:
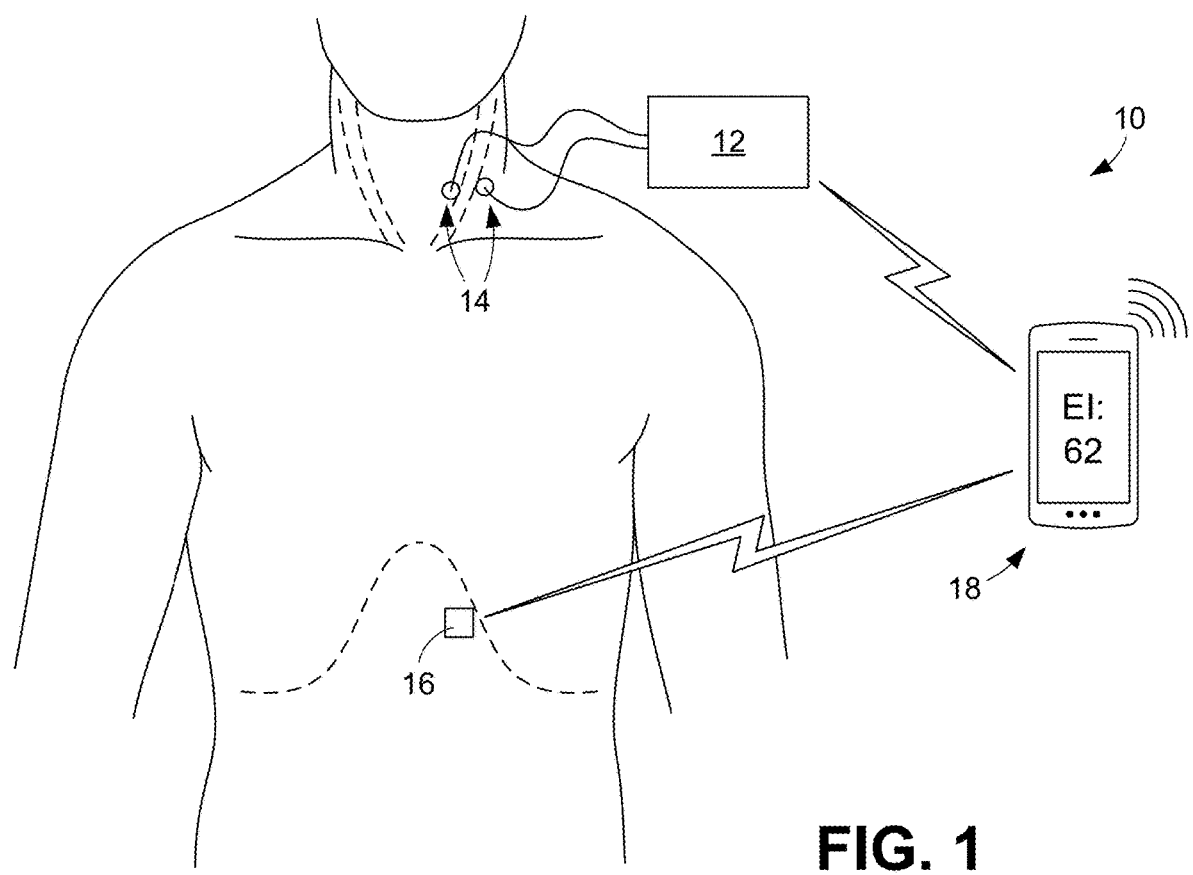
FIG. 1 is a schematic view of an embodiment of a system for assessing respiratory function, shown applied to a human subject.

As indicated above, the respiratory function assessment systems described herein combine phrenic nerve stimulation and diaphragm accelerometry to evaluate respiratory function. FIG. 1 illustrates an example respiratory function assessment system 10. As shown in that figure, the system 10 comprises an electrical stimulation device 12, stimulation electrodes 14 that are connected to the electrical stimulation device with wires, a movement sensor 16, and a controller 18.

Figure 2:
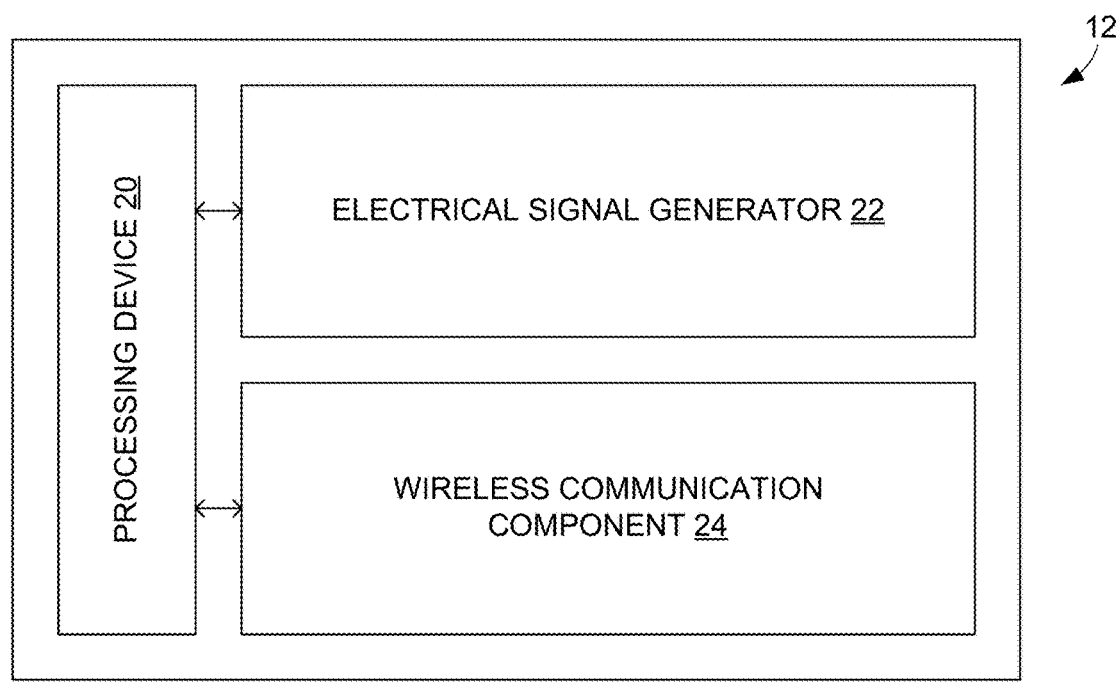
FIG. 2 is a block diagram of an example embodiment of an electrical stimulation device of the system shown in FIG. 1.

The electrical stimulation device 12 is configured to generate electrical stimulation in the form of current waveforms (or simply "stimulation current" or "current") that can be transmitted to the stimulation electrodes 14 for application to a subject's neck. FIG. 2 is a block diagram of an example embodiment for the electrical stimulation device 12. As shown in that figure, the electrical stimulation device 12 can include, among other components, a processing device 20, an electrical current generator 22, and a wireless communication device 24. The processing device 20 is configured to control operation of the electrical stimulation device 12, the electrical current generator 22 is configured to generate the current that is transmitted to the electrodes 14, and the wireless communication device 24 is configured to receive wireless commands from the controller 18.

The current that is generated by the electrical current generator 22 is intense enough to produce a vigorous stimulus to the subject's diaphragm without creating discomfort or pain. In some embodiments, the electrical current generator 22 produces waveforms having a magnitude of approximately 25 to 70 mA and a frequency of approximately 1 to 7 Hz (e.g., 5 Hz). In some embodiments, the waveforms can be biphasic or alternating phasic square waveforms having a periodicity of approximately 100 to 200 μs.

In some embodiments, the wireless communication device 24 is configured to use a short-range wireless technology standard, such as Bluetooth, that is suitable for short-range data transfer between devices. Accordingly, the wireless communication device 24 can at least receive commands from the controller 18 that instruct the electrical stimulation device 12 when to start and stop the generation of current that is to be applied to the subject's neck.

With reference back to FIG. 1, the stimulation electrodes 14 are configured for placement on the subject's neck. More particularly, the electrodes 14 can be applied to the surface of the skin of the neck on opposite sides of the underlying sternocleidomastoid muscle (represented in dashed lines) near the base of the front of the neck. When properly positioned, the electrodes 14 are also positioned on opposite sides of one of the subject's phrenic nerves, which is innervated with the diaphragm. In some embodiments, the electrodes 14 can be manually positioned on the subject's neck by a trained technician. Correct placement of the electrodes 14 can be confirmed by observing and/or measuring movement of the abdomen while current is applied to the phrenic nerve. It is noted that, in some embodiments, the system 10 can further comprise means for maintaining the positions of the electrodes 14 on the subject's neck. For example, the electrodes can be held in place by a strap or band that wraps around the neck, a clamp that grips the sternocleidomastoid (see the description of FIG. 6 below), or adhesive that adheres the electrodes to the surface of the subject's skin.

As shown in FIG. 1, the movement sensor 16 is applied to the subject's abdomen at a point just below the ribcage and a few centimeters to the side of the subject's sagittal plane. When placed in that position, the movement sensor 16 can sense movements of the abdomen that result from contractions of the diaphragm. Such contractions are short in duration and, therefore, may be referred to as muscle "twitches." In some embodiments, the movement sensor 16 can be held in place with adhesive.

Figure 3:
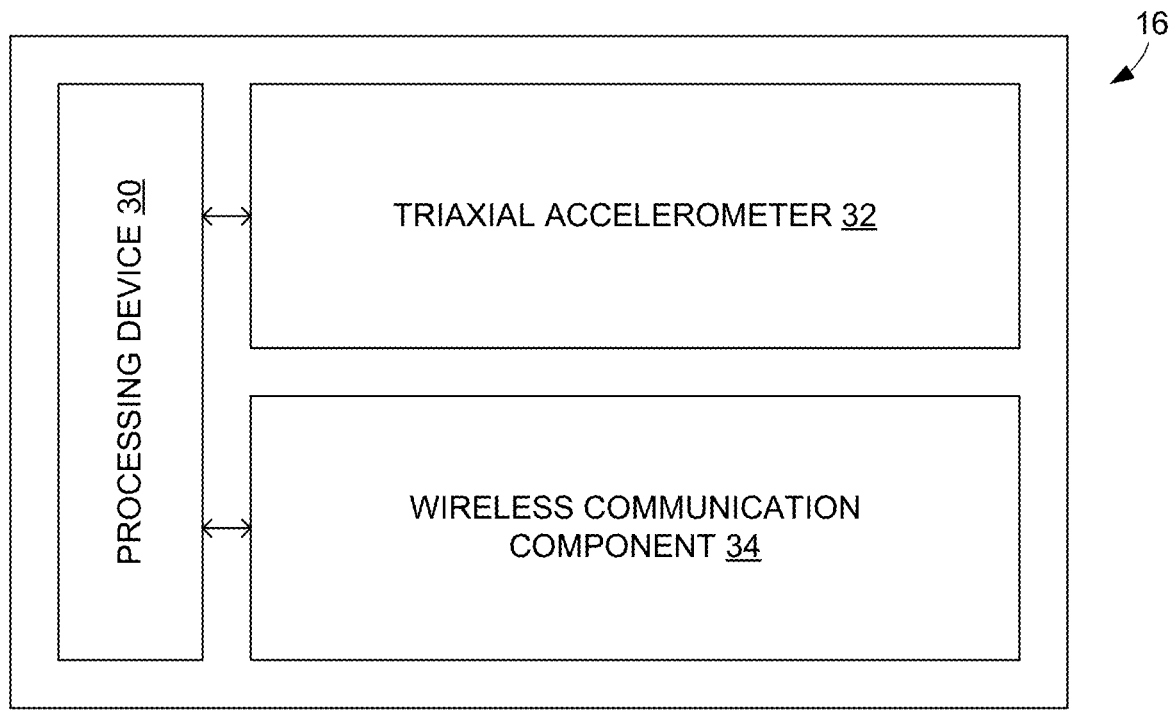
FIG. 3 is a block diagram of an example embodiment of movement sensor of the system shown in FIG. 1.

FIG. 3 is a block diagram of an example embodiment of the movement sensor 16. As shown in that figure, the movement sensor 16 can include, among other things, a processing device 30, a triaxial accelerometer 32, and a wireless communication device 34. The processing device 30 is configured to control operation of the movement sensor 16, the triaxial accelerometer 32 is configured to simultaneously measure accelerations in three orthogonal directions, and the wireless communication device 34 is configured to wirelessly transmit acceleration measurements to the controller 18 for analysis and storage. Although the movement of the abdomen in response to stimulation of the phrenic nerve primarily occurs in a single direction (e.g., upward when the subject is lying on his or her back), it has been determined that measuring accelerations in each of three orthogonal directions increases the accuracy of the measurements and, therefore, the respiratory function assessment. In some embodiments, the accelerometer 32 can be configured to measure accelerations at a sampling frequency of approximately 200 to 400 Hz.

Like the wireless communication device 24 of the electrical stimulation device 12, the wireless communication device 34 can be configured to use a short-range wireless technology standard, such as Bluetooth. With such communication capabilities, the movement sensor 16 can transmit in real-time accelerations of the abdomen to the controller 18.

Figure 4:
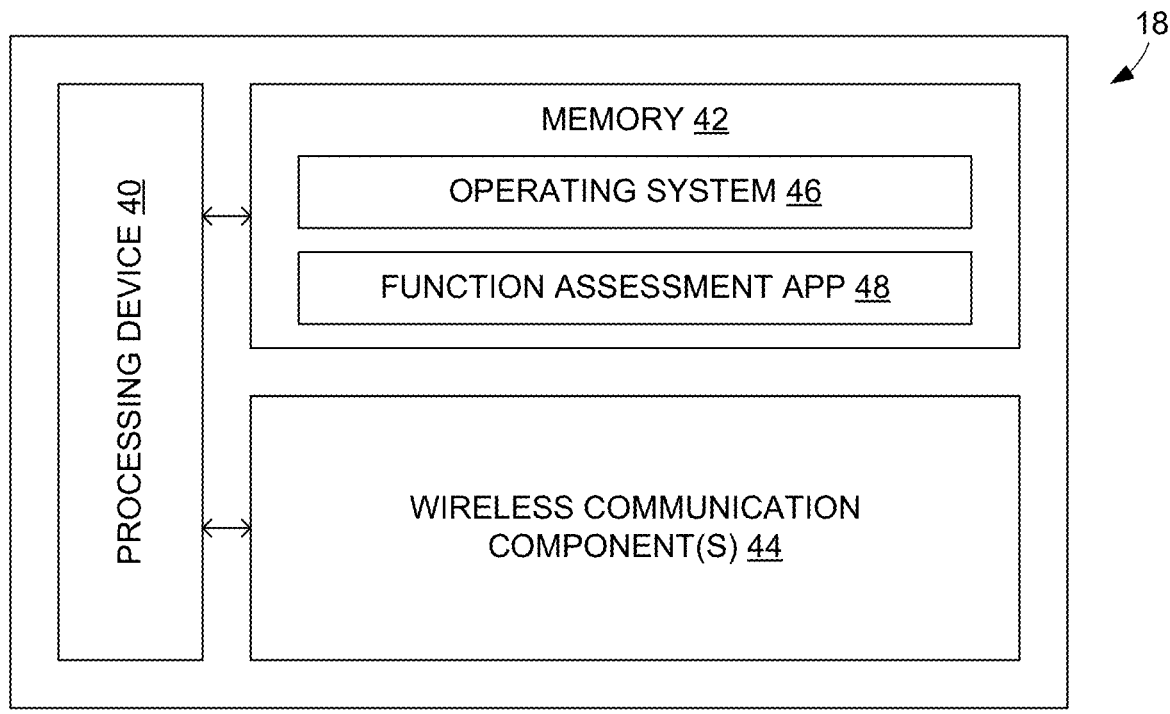
FIG. 4 is a block diagram of an example embodiment of a controller of the system shown in FIG. 1.

As described above, the controller 18 can take the form of a portable, wireless computing device. In the example embodiment shown in FIG. 1, the controller 18 takes the form of a smart phone or tablet device. FIG. 4 is a block diagram of an example embodiment of the controller 18. As shown in that figure, the controller 18 can include, among other things, a processing device 40, memory 42, and one or more wireless communication devices 44. The processing device 40 controls the operation of the controller 18. It does this by executing code stored within the memory 42 (a computer-readable medium) that, in some embodiments, can be integrated with the processing device 40. As shown in FIG. 4, the memory 42 at least stores an operating system 46 and a function assessment application, or "app," 48.

The function assessment app 48, which comprises computer-executable instructions that may form part of one or more algorithms, is configured to control endurance test sessions that are used to assess a subject's respiratory function. Therefore, the assessment app 48 both initiates the test sessions (e.g., upon receiving a command to do so entered by a user on the controller 18) by commanding the electrical stimulation device 12 to start generating the current that is delivered to the subject with the stimulation electrodes 14, and commands the electrical stimulation device to cease generating the current once the full duration of the test session has elapsed. In some embodiments, each test session can have a duration of approximately 2 to 10 minutes (e.g., 5 minutes).

In addition to controlling the test sessions and receiving/storing the acceleration data, the assessment app 48 analyzes the acceleration data to evaluate the activity of the diaphragm and generate an objective measure of the subject's respiratory function. In some embodiments, the assessment app 48 calculates a numerical endurance index that is based on both the magnitude of the diaphragm twitches (accelerations) at the beginning of the test and the magnitude of the twitches near the end of the test. With that data, a numerical endurance index, in the form of a number from 0 to 100, can be generated that quantifies the percentage of the diaphragm that did not fatigue over the course of the test session. Notably, if desired, the quantification of the respiratory function could be presented as a fatigue index, which is the inverse of the endurance index and quantifies the percentage of the diaphragm that did fatigue over the course of the test session.

For the controller 18, the wireless communication devices 44 can comprise a device that is configured to use a short-range wireless technology standard, such as Bluetooth, as well as one or more devices that are configured to transmit and receive data over a computer network using as a Wi-Fi and/or cellular network. In such cases, the controller 18 can not only receive acceleration data from the movement sensor 16 but also transmit that data onto other computing devices over a network, such as to a server connected to the Internet.

An example embodiment of a respiratory function assessment system having been described above, an example method for assessing a subject's respiratory function using the system will now be described.

When an assessment is to be performed, the subject is positioned on an examination table or other appropriate horizontal surface in a supine position with a technician who will be administering the endurance test session positioned to the subject's side for phrenic nerve access. The technician can be positioned on the subject's left or right side as there is no physiological difference between the left or right hemi-diaphragms. Once the subject and technician are in place, the technician applies the stimulation electrodes to opposite sides of the nearest phrenic nerve, which lies underneath the sternocleidomastoid muscle. In some embodiments, one electrode can be placed in between the two origins of the sternocleidomastoid (i.e., the manubrium of the sternum and the medial clavicle), while the other electrode can be moved within the posterior triangle until the phrenic nerve is located. A small amount of pressure can be applied to the electrodes in the area to improve activation of the phrenic nerve.

The stimulation intensity necessary to produce a vigorous but submaximal stimulus can next be determined. As noted above, this intensity is typically in the range of approximately 25-70 mA, which is generally considered to be tolerable by subjects. Next, the movement sensor is placed on the upper abdomen approximately 8 to 10 cm below the xyphoid process and approximately 2 cm lateral of the subject's sagittal plane. Correct placement of the electrodes can be confirmed by delivering current to the electrodes while observing the abdomen to detect twitching movements.

The endurance test protocol involves providing several (e.g., 5) continuous minutes of electrical stimulation (current) at an appropriate (e.g., 5 Hz) stimulation frequency. When the current is applied to the phrenic nerve, the diaphragm twitches and causes movement of the abdomen, which are measured in the form of accelerations in three orthogonal directions. As the accelerometer of the movement sensor is tri-axial, the accelerometer produces an acceleration vector for each twitch that represents the accelerations in each of the three directions.

Figure 5A:
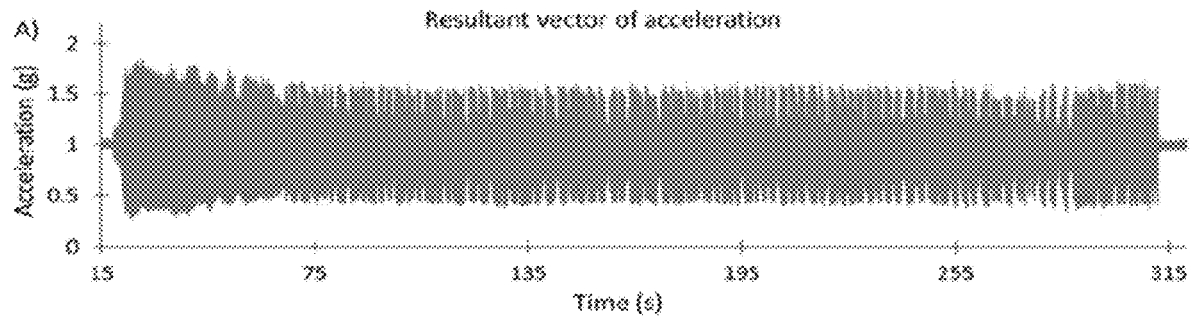
FIG. 5A is a graph that shows example resultant vector magnitudes from the three axes (x, y, z) collected by the accelerometer during diaphragm endurance testing.
Figure 5B:
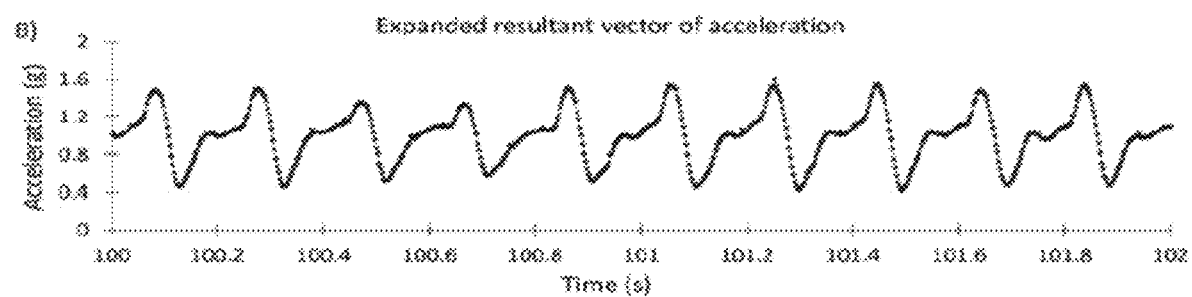
FIG. 5B is a graph that shows two seconds of individual twitches from the 3-axis data of FIG. 5A.
Figure 5C:
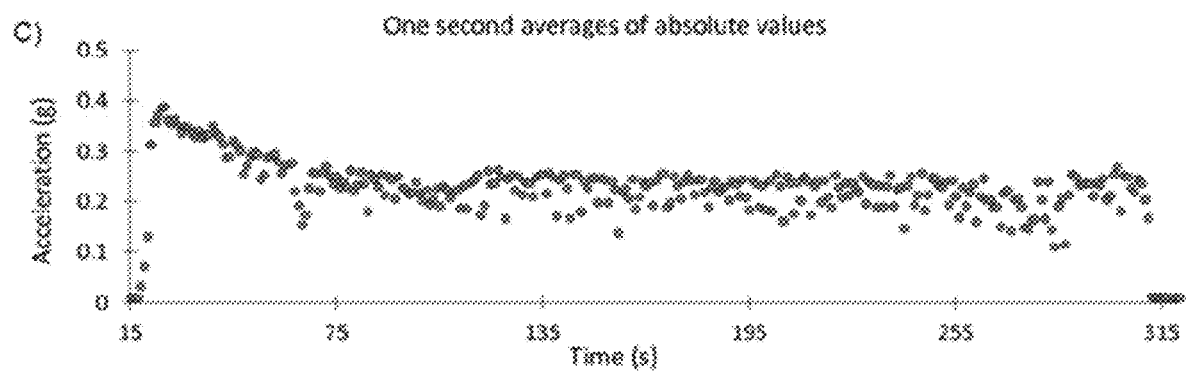
FIG. 5C is a graph that shows 400 point averages of the absolute values of the data of FIG. 5A.

The vectors are converted into absolute values and the maximum peak-to-peak acceleration is recorded for each diaphragm twitch. FIGS. 5A-5C present representative acceleration data that was measured and stored by an assessment system similar to that shown in FIG. 1. FIG. 5A is a graph that shows the resultant vector magnitude (in terms of earth's gravity, g's) collected by the accelerometer as a function of time from an electrical stimulus having a frequency of 5 Hz. FIG. 5B is a graph that shows a two-second portion of the measured vector magnitudes shown in FIG. 5A so that individual twitches of the diaphragm can be seen. FIG. 5C is a graph that shows a 400-point average of the absolute values of the measured accelerations. In this example, the sampling rate of the accelerometer was 400 Hz such that each point in the graph of FIG. 5C is the average of 400 points collected in one second.

Once of the endurance test session has been completed and all of the acceleration data has been collected, the endurance index for the diaphragm, $EI_{dpm}$, can be calculated by dividing the average vector magnitude of the final 20 seconds of test data ($V_{end}$) by the average vector magnitude of the highest three consecutive peaks during the first 30 seconds ($V_{peak}$) and then multiplying by 100:

$$EI_{dpm} = (V_{end} / V_{peak}) \times 100 \qquad \text{Equation 1}$$

The resulting $EI_{dpm}$ is a percentage that estimates the percentage of the diaphragm that did not fatigue as a consequence of the various twitches. Notably, the highest three consecutive peaks are used to determine $V_{peak}$ to account for potentiation (i.e., muscle warm-up) of the diaphragm. As $EI_{dpm}$ estimates the percentage of muscle fatigue of the diaphragm as a whole, which results from partial or complete fatigue of the various individual fibers of the muscle (the diaphragm's muscle fibers are of the fast, low-oxidative type), the higher $EI_{dpm}$, the greater the endurance of the diaphragm and, therefore, the better the subject's respiratory function. If $EI_{dpm}$ is low, however, the diaphragm became highly fatigued as a consequence of the twitches and, therefore, the subject would not be able to sustain normal, unassisted breathing over time and would be at risk of respiratory failure. Although there is no particular number above which a subject's respiratory function should be considered to be "good" and below which the subject's respiratory function should be considered to be "bad," generally speaking, an $EI_{dpm}$ of approximately 35 to 40 and higher is likely indicative of adequate respiratory function.

The above-described endurance test is useful for determining when someone is at risk for respiratory failure. In addition, it is useful for evaluating the outcome of rehabilitation programs. In some embodiments, the test can be performed on patient populations with a history of or risk factors for respiratory failure. This includes persons in intensive care units, persons who need to be weaned off of ventilators, and persons with partial paralysis of their respiratory muscles (e.g., resulting from a spinal cord injury, Friedreich's ataxia, etc.).

While the focus of the disclosure to this point has been on assessment of a subject's respiratory function, it is noted that the system, or one like it, can also be used to monitor for damage to the phrenic nerve during medical and surgical procedures. For example, phrenic nerve damage is a relatively common consequence of cryoablation surgery for atrial fibrillation as well as for other surgical procedures. Such damage can critically reduce respiratory function for months while the phrenic nerve heals. A standardized system and protocol that produces objective, quantifiable feedback (such as the above-described index) could be used to prevent or at least minimize such phrenic nerve damage.

In some embodiments, the health and functioning of the phrenic nerve can be monitored during a medical or surgical procedure by applying stimulation electrodes and a movement sensor to the patient in similar manner to that described above. Twitch stimulation current can then applied as described above. Depending upon the nature of the procedure, phrenic nerve stimulation could alternatively be performed using electrodes placed on the phrenic nerve via the venous vasculature.

During critical parts of the procedure, the phrenic nerve can be stimulated at a low frequency, such as 1 Hz, and the measured acceleration data can be analyzed by the controller in real time. In some embodiments, this analysis can comprise simply monitoring for when accelerations fall below a predetermined floor established for the individual upon which the procedure is being performed. In such a case, the medical professional performing the procedure can set the floor after baseline measurements for the individual's twitch accelerations have been obtained prior to the procedure. In other embodiments, an index (e.g., percentage) similar to the endurance index can be calculated in real time. In either case, the system can warn the medical professional when the acceleration data indicates that the phrenic nerve has been adversely affected as evidenced by a substantial reduction in diaphragm activity during nerve stimulation. For example, the system can initiate an audible and/or visual alarm that alerts the medical professional of the situation so that he or she can halt the procedure and avoid serious damage to the phrenic nerve.

Such a test can also be performed after a medical or surgical procedure. For example, an acceleration intensity curve can be generated by stimulating the phrenic nerve at 1 or 2 Hz starting using a current magnitude that produces vigorous abdominal movement, and then gradually reducing the stimulus over one, two, or a few minutes to zero current. A current-to-acceleration curve can then be generated and used to determine if nerve damage has occurred.

In view of this alternative application, the above-disclosed respiratory function assessment system can more generally be referred to as an "assessment system" that can be used to assess not only the respiratory function of a subject but also the status of a patient's phrenic nerve during a medical or surgical procedure.

Figure 6A:
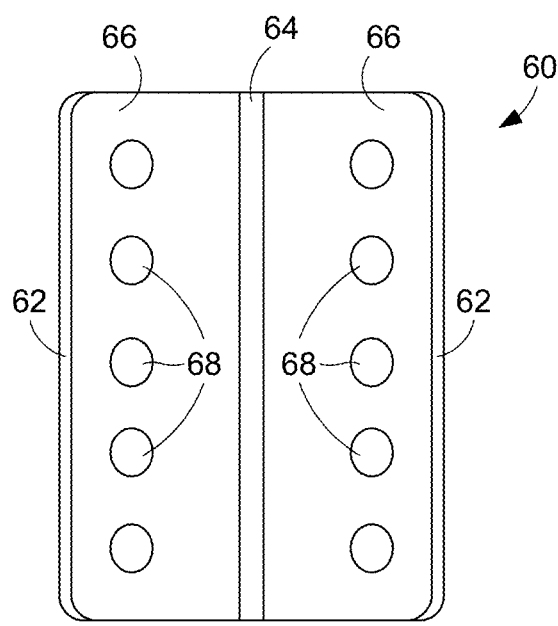
FIGS. 6A and 6B are front and top views, respectively, of an example embodiment of a stimulation electrode device that can be used in the system shown in FIG. 1.
Figure 6B:
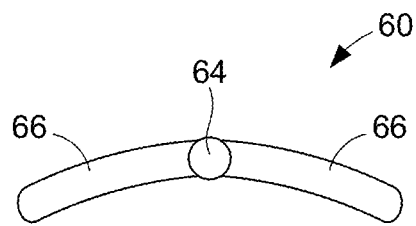

As identified above, the stimulation electrodes can, in some embodiments, take the form of a clamp that is configured to grip the sternocleidomastoid. FIGS. 6A and 6B illustrate an example of such a clamp 60. As shown in those figures, the clamp 60 can comprise two opposed arms 62 that are pivotally connected to each other with a hinge 64. In some embodiments, the hinge 64 can incorporate a torsion spring (not visible) that biases the arms 62 toward each other so that the clamp 60 can be attached to the sternocleidomastoid of a subject or patient and will stay in place under the force of the spring.

With specific reference to FIG. 6A, the inside surface 66 of each arm 62 comprises an array of stimulation electrodes 68 that can be used to deliver current to the subject's or patient's neck and phrenic nerve. Multiple electrodes 68 are provided to at least partially automate the process of positioning electrodes near the phrenic nerve. In some embodiments, the clamp 60 can be attached to the neck and, in an initial calibration procedure, current can alternately be applied with different pairs of electrodes 68 while accelerations of the abdomen are monitored until a pair of electrodes is identified that are best positioned to stimulate the phrenic nerve. If more than one pair of electrodes 68 are identified that provide stimulation to the phrenic nerve, the pair that provides the greatest amount of stimulation (i.e., the greatest accelerations of the abdomen), can be automatically selected to be used in the test that will follow.

The invention claimed is:

1. An assessment system comprising:
   an electrical stimulation device configured to generate current;
   stimulation electrodes configured to apply the current generated by the electrical stimulation device to a neck of a subject at a location that results in stimulation of a phrenic nerve of the subject;
   a movement sensor configured to sense movement of an upper abdomen of the subject caused by twitching of a diaphragm of the subject responsive to the stimulation of the phrenic nerve; and
   a controller configured to receive data sensed by the movement sensor, analyze the received data to evaluate an extent to which the diaphragm fatigues over the course of an endurance test during which the phrenic nerve is stimulated for several minutes, and generate an assessment of the subject's respiratory function or phrenic nerve.

2. The system of claim 1, wherein the electrical stimulation device further comprises a wireless communication device with which the electrical stimulation device can receive wireless commands from the controller.

3. The system of claim 1, wherein the movement sensor comprises an accelerometer that measures accelerations of the abdomen associated with the twitches of the diaphragm.

4. The system of claim 3, wherein the accelerometer is a triaxial accelerometer that measures accelerations of the abdomen in three orthogonal directions.

5. The system of claim 3, wherein the movement sensor further comprises a wireless communication device with which the movement sensor can wireless transmit the measured accelerations to the controller.

6. The system of claim 1, wherein the controller comprises a portable, wireless computing device.

7. The system of claim 6, wherein the portable, wireless computing device is a smart phone or a tablet device.

8. The system of claim 1, wherein the controller generates an assessment by calculating an endurance index that estimates a percentage of the diaphragm that did not fatigue over the course of the endurance test.

9. The system of claim 8, wherein calculating an endurance index comprises dividing an average acceleration vector magnitude measured during an initial portion of the endurance test by an average of the magnitude of the highest consecutive acceleration vectors measured during a final portion of the endurance test, and then multiplying by 100.

10. The system of claim 1, wherein the controller is further configured to control operation of the electrical stimulation device.

11. The system of claim 1, wherein the controller is configured to analyze the received acceleration data to monitor for damage to the phrenic nerve during a medical or surgical procedure.

12. The system of claim 11, wherein the controller is configured to determine that the phrenic nerve may have been damaged when a substantial reduction in abdomen accelerations occurs, which is indicative of a reduction of diaphragm activity.

13. The system of claim 1, wherein the electrodes comprise part of a clamp that is configured to grip a sternocleidomastoid of the subject.

14. The system of claim 13, wherein the clamp comprises opposed arms, each arm having an inside surface that comprises an array of electrodes, wherein pairs of electrodes can be alternately used to apply current to the neck to determine which pair provides the greatest amount of stimulation to the phrenic nerve.

15. The system of claim 1, wherein the controller is configured to analyze the received acceleration data to monitor for damage to the phrenic nerve during a medical or surgical procedure.

16. The system of claim 15, wherein the controller is configured to determine that the phrenic nerve may have been damaged when a substantial reduction in abdomen accelerations occurs, which is indicative of a reduction of diaphragm activity.

17. An assessment system comprising:
   an electrical stimulation device configured to generate current, the electrical stimulation device including an electrical current generator that generates current waveforms having a magnitude of approximately 25 to 70 mA and a frequency of approximately 1 to 7 Hz;
   stimulation electrodes configured to apply the current generated by the electrical stimulation device to a neck of a subject at a location that results in stimulation of a phrenic nerve of the subject;
   a movement sensor configured to sense movement of an upper abdomen of the subject caused by twitching of a diaphragm of the subject responsive to the stimulation of the phrenic nerve; and
   a controller configured to receive data sensed by the movement sensor, analyze the received data to evaluate the activity of the diaphragm, and generate an assessment of the subject's respiratory function or phrenic nerve.

18. The system of claim 17, wherein the movement sensor comprises a triaxial accelerometer that measures accelerations of the abdomen in three orthogonal directions.

19. The system of claim 17, wherein the controller generates an assessment by calculating an endurance index that estimates a percentage of the diaphragm that did not fatigue over the course of the endurance test.

20. The system of claim 19, wherein calculating an endurance index comprises dividing an average acceleration vector magnitude measured during an initial portion of the endurance test by an average of the magnitude of the highest consecutive acceleration vectors measured during a final portion of the endurance test, and then multiplying by 100.

* * * * *